United States Patent [19]
Park et al.

[11] Patent Number: 6,039,054
[45] Date of Patent: Mar. 21, 2000

[54] DENTAL FLOSS

[75] Inventors: Edward H. Park, Sharon; Philip Sweeney, Taunton, both of Mass.

[73] Assignee: Gillette Canada Company, Halifax, Canada

[21] Appl. No.: 09/159,167

[22] Filed: Sep. 23, 1998

[51] Int. Cl.[7] .................................................. A61C 15/00
[52] U.S. Cl. ........................ 132/321; 132/323; 132/329
[58] Field of Search .................................. 132/321, 323, 132/329, 308, 309

[56] References Cited

U.S. PATENT DOCUMENTS

| | | | |
|---|---|---|---|
| 2,381,142 | 4/1942 | Stonehill | 18/59 |
| 2,667,443 | 5/1949 | Ashton | 167/93 |
| 3,423,923 | 1/1969 | Hume | 57/140 |
| 3,531,368 | 9/1970 | Okamoto et al. | 161/173 |
| 3,558,419 | 1/1971 | Okazaki et al. | 161/173 |
| 3,594,266 | 7/1971 | Okazaki et al. | 161/173 |
| 3,645,819 | 2/1972 | Fujii et al. | 156/148 |
| 3,679,541 | 7/1972 | Davis et al. | 161/175 |
| 3,699,979 | 10/1972 | Muhler et al. | 132/89 |
| 3,761,348 | 9/1973 | Chamberlin | 161/173 |
| 3,771,536 | 11/1973 | Dragan | 132/89 |
| 3,789,858 | 2/1974 | Pesce | 132/89 |
| 3,800,812 | 4/1974 | Jaffe | 132/89 |
| 3,837,351 | 9/1974 | Thornton | 132/89 |
| 3,838,702 | 10/1974 | Standish et al. | 132/89 |
| 3,897,795 | 8/1975 | Engel | 132/89 |
| 3,943,949 | 3/1976 | Ashton et al. | 132/89 |
| 3,957,067 | 5/1976 | Ferraro et al. | 132/89 |
| 3,968,307 | 7/1976 | Matsui et al. | 428/373 |
| 4,033,365 | 7/1977 | Klepak et al. | 132/89 |
| 4,122,658 | 10/1978 | Morioka et al. | 57/140 |
| 4,350,006 | 9/1982 | Okamoto et al. | 57/250 |
| 4,414,990 | 11/1983 | Yost | 132/91 |
| 4,447,489 | 5/1984 | Linhart et al. | 428/225 |
| 4,554,154 | 11/1985 | White | 424/16 |
| 4,583,564 | 4/1986 | Finkelstein et al. | 132/91 |
| 4,836,226 | 6/1989 | Wolak | 132/321 |
| 4,911,927 | 3/1990 | Hill et al. | 424/443 |
| 4,974,615 | 12/1990 | Doundoulakis | 132/321 |
| 5,076,300 | 12/1991 | Mayfield | 132/321 |
| 5,098,711 | 3/1992 | Hill et al. | 424/401 |
| 5,165,913 | 11/1992 | Hill et al. | 424/49 |
| 5,372,885 | 12/1994 | Tabor et al. | 428/373 |
| 5,413,127 | 5/1995 | Hill | 132/321 |
| 5,433,226 | 7/1995 | Burch | 132/321 |
| 5,439,741 | 8/1995 | Gibbon et al. | 428/377 |
| 5,479,952 | 1/1996 | Zachariades et al. | 132/321 |

*Primary Examiner*—John J. Wilson
*Assistant Examiner*—Robyn K. Doan
*Attorney, Agent, or Firm*—Fish & Richardson P.C.

[57] ABSTRACT

Dental flosses are provided that include a foam. Preferred flosses include a foam outer layer and a reinforcing core and may be formed as a multicomponent coextruded filament.

43 Claims, 6 Drawing Sheets

DENTAL FLOSS

BACKGROUND OF THE INVENTION

The present invention relates to dental flosses and methods for making dental floss.

Tooth decay and dental disease can be caused by bacterial action resulting from the formation of plaque about the teeth and/or the entrapment of food particles in interstices between the teeth. Removal of plaque and entrapped food particles reduces the incidence of caries, gingivitis, and mouth odors as well as generally improving oral hygiene. Conventional brushing has been found to be inadequate for removing all entrapped food particles and plaque. To ensure adequate dental hygiene, flossing is recommended.

Dental flosses often include additives such as flavors or colors.

SUMMARY OF THE INVENTION

The present invention relates to dental flosses that include a foam. These dental flosses are comfortable to use, and have a surface texture that provide good perceived cleaning during flossing. It is also believed that if the foam is an open cell foam, i.e., a foam in which at least some of the cells at the surface of the foam have an opening that communicates with the surface to form an open cavity at the surface, the cells may create a slight vacuum when the floss decompresses during removal from between the teeth, potentially sucking the tiny particles of debris that are loosened by flossing into the cells. Moreover, the foam can be used to deliver a substance to the mouth during flossing, for example a flavor or therapeutic agent.

Preferred flosses are formed of a monofilament, and have a diameter of from about 0.02 to 0.20 inch. The filament is preferably a multicomponent coextruded filament. By "multicomponent", we mean that the filaments have two or more components; by "coextruded", we mean that at least two of the components are present in the form of substantially separate phases having a distinct interface between them, rather than being intermixed. These filaments are preferably formed by processes which are referred to in the art as "coextrusion", but the term "multicomponent coextruded", as used herein, encompasses filaments having the structure described above which are manufactured by other processes.

In one aspect, the invention features a dental floss that includes two or more components selected to provide desired properties to the floss, one of the components being a foam. For example, the filaments may include an inner core selected to provide strength to the floss, and an outer foam layer. The foam layer can be modified to provide a desired surface property, e.g., softness or abrasiveness.

In another aspect, the invention features improved dental flosses that include a foam containing an additive, e.g., a color, fragrance, flavor or active ingredient, which is releasable from the floss. Some preferred flosses include a combination of components selected to give the floss desired properties, e.g., surface properties such as softness and texture combined with good tensile strength. The additive-containing component(s) may be water-soluble, to allow the additive to leach from the floss during use. The additive may be provided as supplied, in microencapsulated form, or adsorbed or absorbed onto another additive, e.g., a particulate filler. The additive can also be provided on charged microspheres, as described in U.S. Pat. No. 5,300,290, the disclosure of which is incorporated herein by reference.

Advantageously, additives can be incorporated into the flosses of the invention during manufacture of the filaments, rather than applying the additives later during separate coating steps. This not only reduces the number of processing steps, but also reduces the amount of additive needed.

The invention further features methods of making filaments by (a) coextruding two or more polymers through a multicomponent die to form a multicomponent filament; and (b) foaming one of the polymers during or prior to coextrusion to provide the filament with a foamed outer layer.

Additionally, the invention features methods of flossing the teeth of a mammal, e.g., a human, by inserting between two teeth of the mammal a length of a dental floss of the invention.

The term "dental floss", as used herein, is defined to include dental flosses, dental tapes, and similar articles.

Other features and advantages of the invention will be apparent from the drawings, the following Detailed Description, and the claims.

DESCRIPTION OF THE PREFERRED EMBODIMENT

Preferred flosses are formed of a multicomponent filament formed of two or more polymeric components, at least one of which is foamed.

Figure 1:
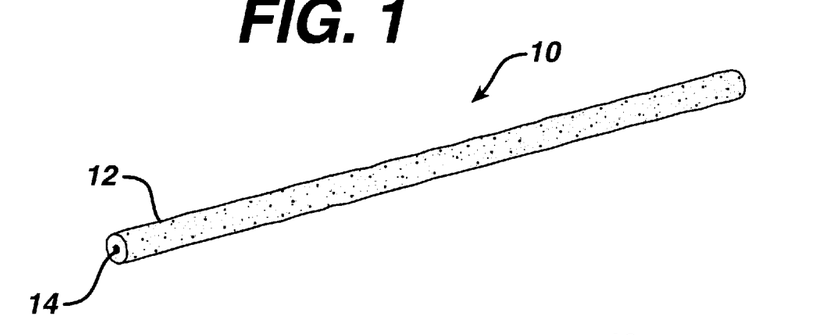
FIG. 1 is a highly enlarged diagrammatic perspective view of a dental floss according to one embodiment of the invention.

As shown in FIG. 1, a preferred floss 10 includes a foam outer layer 12 that provides the floss with softness and texture. The foam may be an open cell or a closed cell foam, as will be discussed further below. The floss 10 also includes a rein forcing core 14 of a material having a higher tensile strength than that of the foam, to provide the floss with sufficient strength to withstand normal use. Preferred flosses have a tensile strength of at least 2000 g, more preferably 2200 g and most preferably at least 2600 g, using ASTM Method D 2101-93.

Suitable materials for use in the foam outer layer include but are not limited to TPEs (thermoplastic elastomers), e.g., polyether block amides such as those available under the tradename PEBAX from ELF Atochem, polyester elastomers such as those available under the tradename HYTREL from DUPONT, and styrene butadiene block copolymers such as those available under the tradename KRATON from Shell; styrene-propylene block copolymers, such as those commercially available from Kurary under the tradename SEPTON; EVA (ethylene vinyl acetate); polyurethane-based materials (TPUs), such as polymers available from Thermedics, Inc., under the tradenames TECOFLEX and TECOTHANE, from Dow Chemical under the tradename PELLATHAN, and from BASF under the tradename ELASTOLLAN; and polyolefin-based TPEs such as polymers available from DSM Inc. under the tradename SARLINK, and from AES Corp. under the tradename SANTOPRENE. Preferably, the foam outer layer is formed of a foamed thermoplastic elastomer, more preferably a styrene-butadiene-styrene or styrene-ethylene-butadiene-styrene KPATON block copolymer such as those commercially available as product nos. G 6703, G 6713, G 2706 and D 3226, or a polyolefin-based TPE with a built-in foaming agent, such as polymers available from DSM Inc. under the tradename SARLINK Series 4000-8100. Preferred polymers for use in the foam outer layer have a hardness of from 0–85 Shore A, more preferably 0–60 Shore A before foaming. Preferably, foaming reduces the density of the sheath polymer by 5 to 95%, more preferably by 30–50%.

Suitable materials for use in the core include thermoplastic elastomers, e.g., polyether block amides such as those available under the tradename PEBAX from ELF Atochem, polyester elastomers such as those available under the tradename HYTREL from DUPONT, thermoplastic polyurethanes (TPUs), e.g., polymers available from Dow Chemical under the tradename PELLATHAN, and from BASF under the tradename ELASTOLLAN; blends of a TPU with a styrenic-based copolymer, for example a polymer blend available from M.A. Hanna under the tradename HTE 2203; nylon; polyester; polypropylene; other blends of copolymers such as blends of PEBAX MX 1205 and KRATON FG 1901 polymers available from M.A. Hanna; and spinnable polymer fibers such as those available from DuPont under the tradename KEVLAR, and those available from Allied Signal under the tradename SPECTRA. Preferably, the core is formed of a high strength thermoplastic elastomer, such as PEBAX MX 1205, HYTREL 3680, or HANNA HTE 2203 elastomers. Preferably, the core polymer has a hardness of at least 60 Shore A, more preferably a hardness of from about 70 to 90 Shore A, and a sufficiently high tensile strength to provide the dental floss with the desired tensile strength and tear resistance properties.

Preferably, the two components are provided in a volumetric ratio of from about 5:95 to 95:5, more preferably a volumetric ratio of about 40:60 to 60:40, most preferably about 50:50.

The outer foam layer may be modified to be abrasive, to improve the perceived cleaning capability of the floss.

If the outer layer is to include an abrasive, for improved cleaning, preferred abrasives include particles of kaolin, calcium carbonate, zinc oxide, silica, PTFE, or blends of these particles which are compatible. If desired, one or more additives may be absorbed or adsorbed on the surface of the abrasive particles, e.g., by drum drying, spray drying, fluidized bed processing, or other suitable methods as is known in the art.

Other types of particles can be added to the sheath polymer, for example as disclosed in copending application U.S. Ser. No. 08/738,982, the disclosure of which is hereby incorporated herein by reference.

Figure 2:
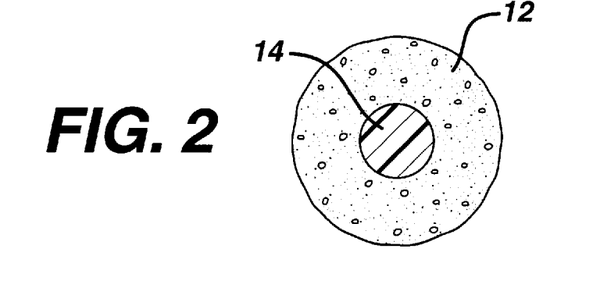
FIGS. 2–2F are cross-sectional views, taken radially, of multicomponent coextruded filaments having various cross-sections.
Figure 2A:
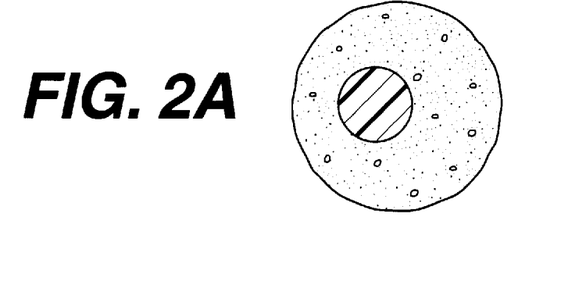
Figure 2B:
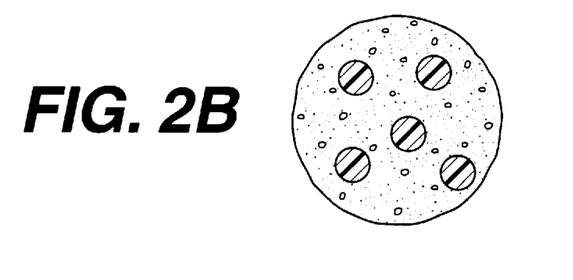
Figure 2C:
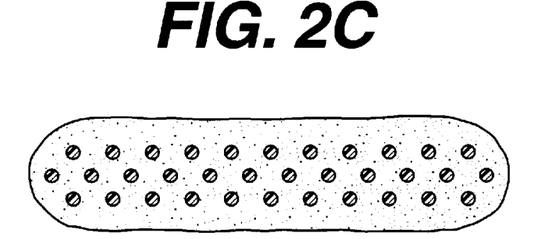
Figure 2D:
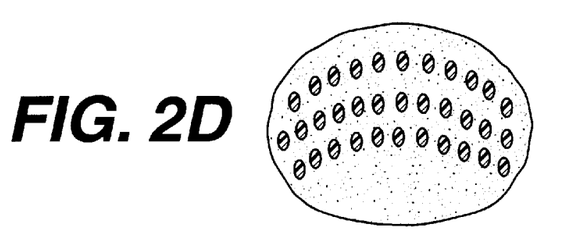
Figure 2E:
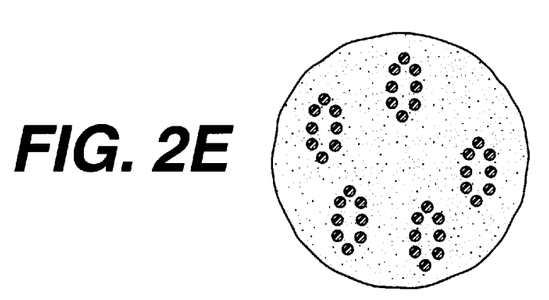
Figure 2F:
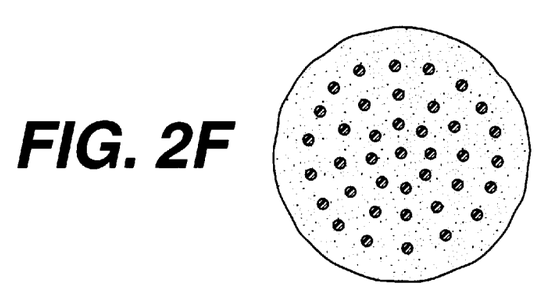

The foam outer layer and the reinforcing core may be provided in any suitable cross-section, e.g., a symmetric sheath/core cross-section (FIGS. 1 and 2), an eccentric sheath/core cross-section (FIG. 2A), or an islands in the sea cross-section (FIGS. 2B–2F). If an islands in the sea cross-section is used, preferably the floss includes from 1 to 200 islands, more preferably 10 to 50 islands, and most preferably 20 to 35 islands. The preferred volumetric ratio of islands to sea is from about 25:75 to 75:25, more preferably about 50:50. Preferably the islands would all have the same diameter and be uniformly distributed. The overall cross-sectional shape of the dental floss 10 can be round, oval, or any other suitable shape. Preferred flosses have a diameter of from about 0.02 to 0.2 inch, more preferably about 0.04 to 0.100 inch.

Specialty flosses can also be formulated to include one or more additives, e.g., a color, fragrance, or active ingredient, in one or both of the components.

For example, the outer foam layer may contain an additive such as chlorhexidine (or a salt thereof), cetyl pyridium achloride (CPC), triclosan, sodium fluoride, flavor (e.g. flavors available from Quest International Fragrances, Mt. Olive, N.J.), fragrance, tooth desensitizer, tooth whitener or other additives suitable for use in dental flosses. Liquid additives are applied to open cell foams after the foaming process, but before the floss is wound. Solid additives are impregnated into open cell foams before the foamed plastic has cooled. Other methods for incorporating additives are described in copending U.S. Ser. No. 08/699,891, the disclosure of which is hereby incorporated herein by reference.

The additive, if desired, can be incorporated in encapsulated form. Encapsulation may be used for thermal protection or moisture protection of the additive, and may be accomplished by any number of conventional techniques such as spray drying, drum drying, spray chilling, coacervation, or solvent evaporation. The additive can also be provided on a charged microsphere, as described in U.S. Pat. No. 5,300,290.

Figure 3:
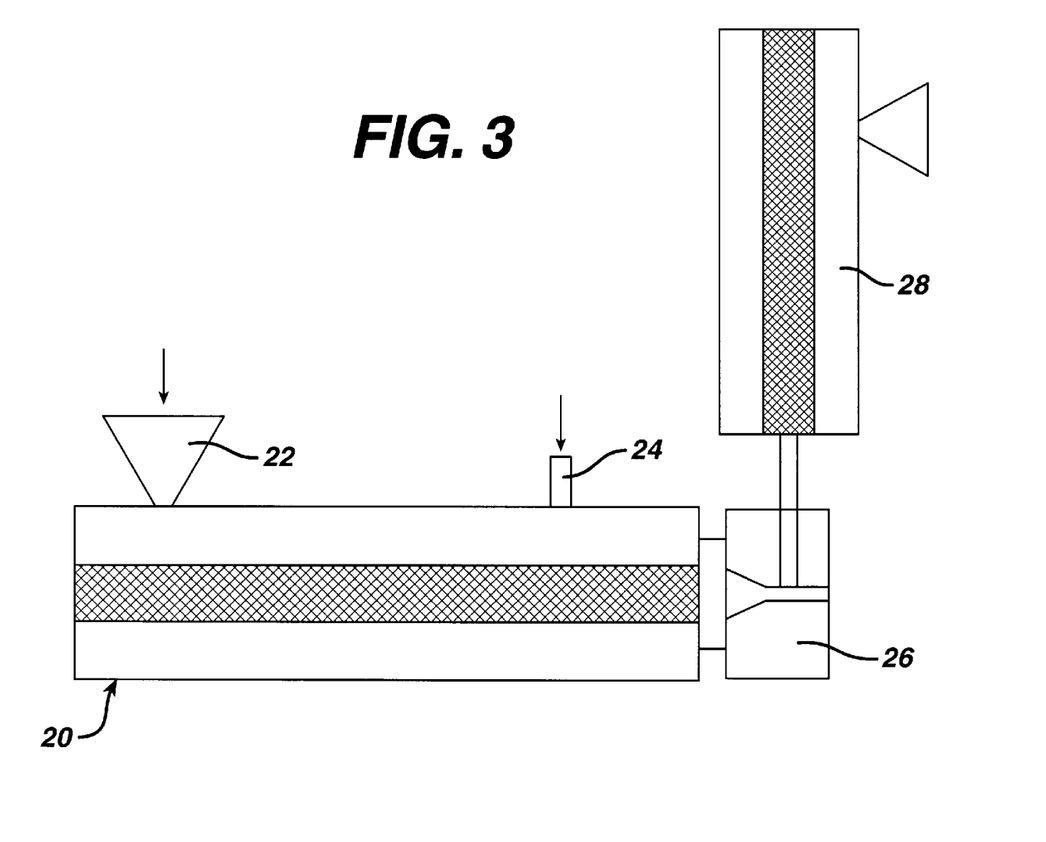
FIG. 3 is a diagrammatic view of an extruder system for making a coextruded dental floss according to one embodiment of the invention.

To form the dental floss, two or more polymers are coextruded through a two component extrusion die to form a bicomponent filament, with at least one of the components being foamed during the manufacturing process. A preferred process is shown in FIG. 3. First, the polymer to be foamed (e.g., a thermoplastic elastomer (TPE)) is introduced into a foam extruder 20 through port 22, with a chemical blowing agent such as a mixture of citric acid and sodium bicarbonate, e.g., a blowing agent available under the tradename HYDROCEROL-BIH from Boehinger Ingelheim, Zupelhern, Germany. Suitable blowing agents are compounds that will decompose at the temperatures encountered in the extruder, and that are safe for use in the mouth. Other suitable chemical blowing agents include azo dicarbonamide, dinitroisopentamethylene tetraamine, sulfonyl hydrazides, p-toluene sulfonyl semicarbazide, 5-phenyltetrazole, diisoprophylhydrazo dicarboxylate, 5-phenyl-3,6-dihydro-1,3,4-oxadiazin-2-one, and sodium borohydride. Preferably from 0.1 to 5% by weight of the blowing agent is added, based on the weight of the polymer to be foamed.

Figure 3A:
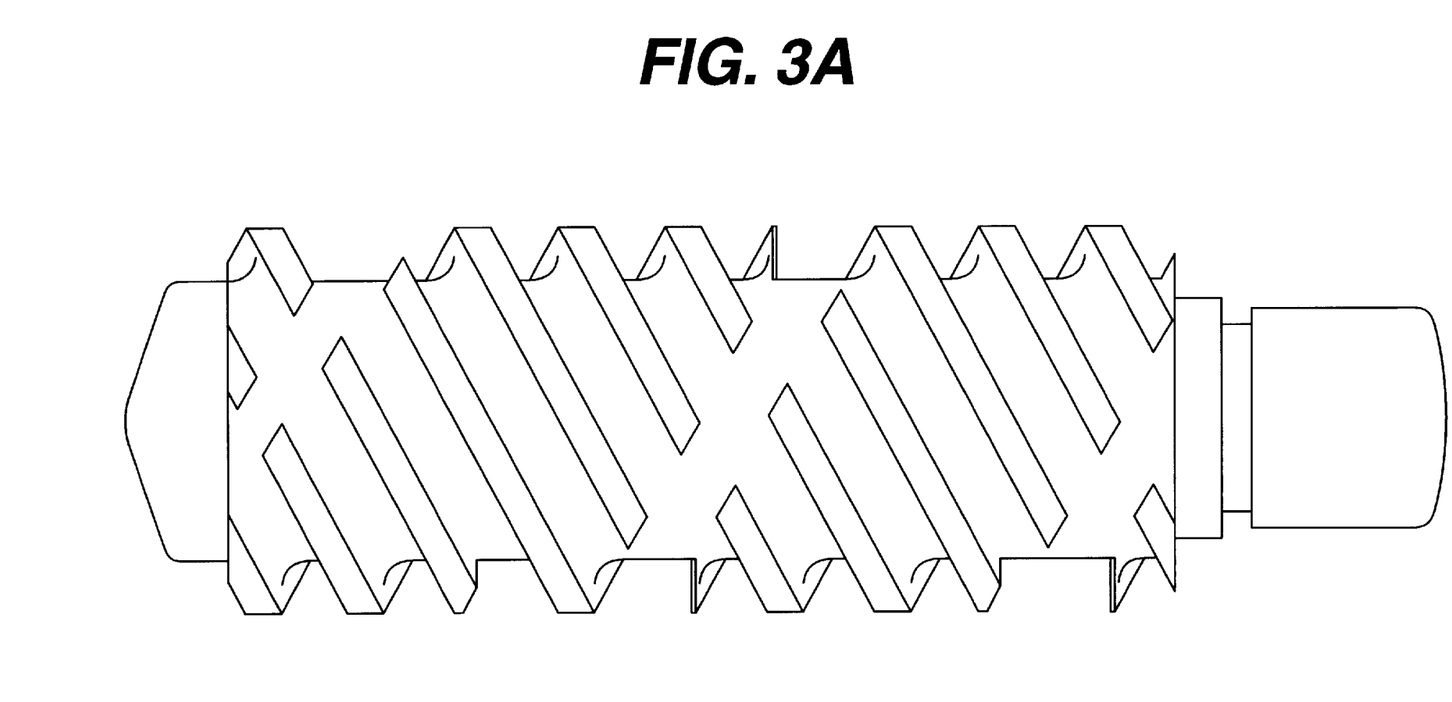
FIG. 3A is a diagrammatic view of a screw mixer suitable for use in the extruder system of FIG. 3.

The foam extruder 20 has a long barrel and includes an intensive screw mixer, to completely mix the blowing agent with the polymer. A suitable screw mixer is shown in FIG. 3A. Preferably the barrel has a length to diameter (L/D) ratio of from about 20:1 to 50:1, preferably about 40:1. A suitable foam extruder is commercially available from Akron Extruder, Ohio.

The foam extruder includes a feeding zone at which a polymer is fed to the extruder (e.g., through a hopper); a melting zone, at which the polymer is heated until liquid; a mixing zone, where a blowing agent is intensively mixed with the polymer, as will be discussed further below; and a compression zone, after which the polymer exits to the die.

Instead of, or in addition to, including a chemical blowing agent, a physical blowing agent, typically a gas (e.g., carbon dioxide, nitrogen or other inert gases), can be introduced into the molten polymer in the foam extruder, through gas port 24. The gas is injected under high pressure, e.g., 100 to 2000 psi, preferably about 600 psi, and mixed with the polymer to dissolve it into the molten polymer. The gas then expands when pressure is released (i.e., when the polymer exits the extruder).

The intensive screw mixer provides an intensive mixing zone positioned immediately after the gas injection port (if a physical foaming agent is to be used) or right after the melting zone (if a chemical blowing agent is to be used) to maximize the mixing of the molten polymer and the gas. The polymer then exits the foam extruder and enters a coextrusion die 26, where it is coextruded with non-foamed polymer exiting a second extruder 28.

Foaming can occur before the polymer exits the foam extruder (in which case the resulting foam will be an open cell foam) or after the polymer exits the foam extruder (in which case the foam will be a closed cell foam). The cell size of the foam can also be varied by changing the process parameters, as is well known in the foam forming field. If greater surface roughness is desired, this can be attained by increasing the foaming temperature.

The compression zone of the foam extruder barrel should be maintained at low temperature to prevent premature foaming in the barrel or die. For example, for a melting zone temperature of 190° C., the temperature of the compression zone is preferably about 170° C. for a KRATON rubber foaming process.

Figure 4:
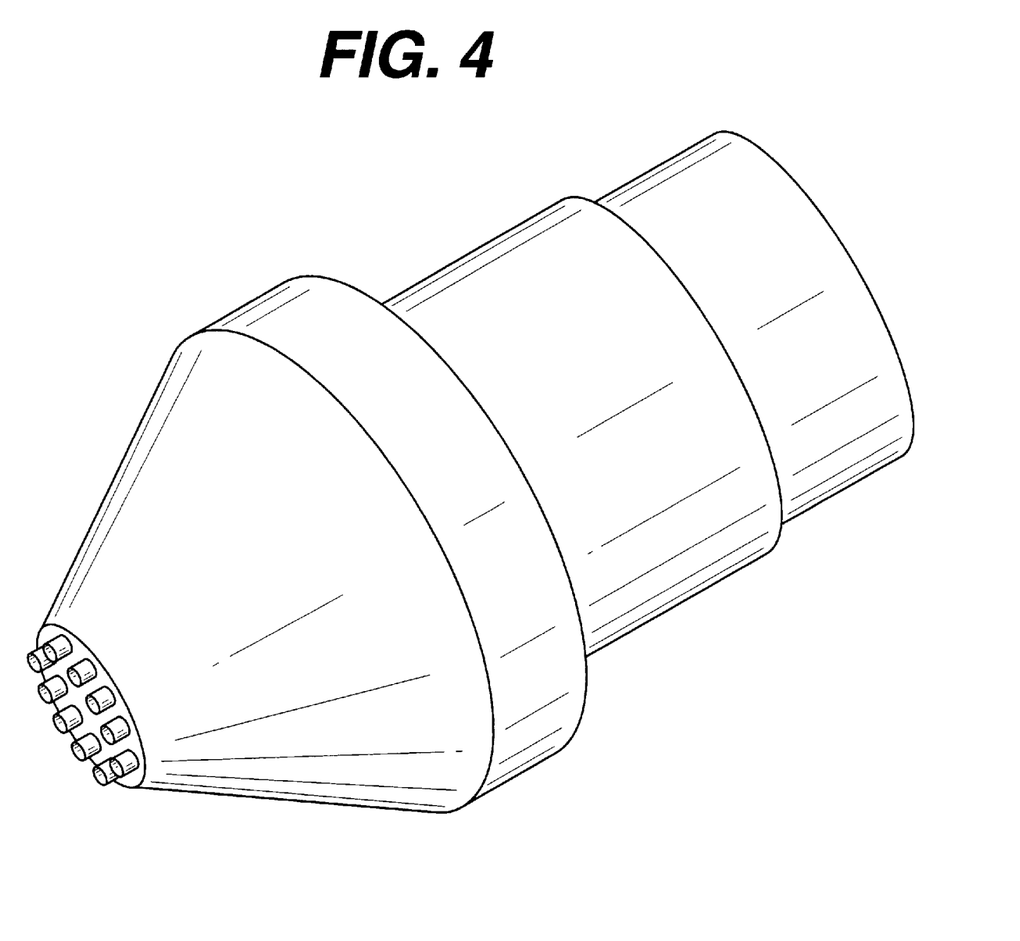
FIGS. 4 and 4A are, respectively, a perspective view and a side cross-sectional view of a coextrusion die suitable for use in the process shown in FIG. 3.
Figure 4A:
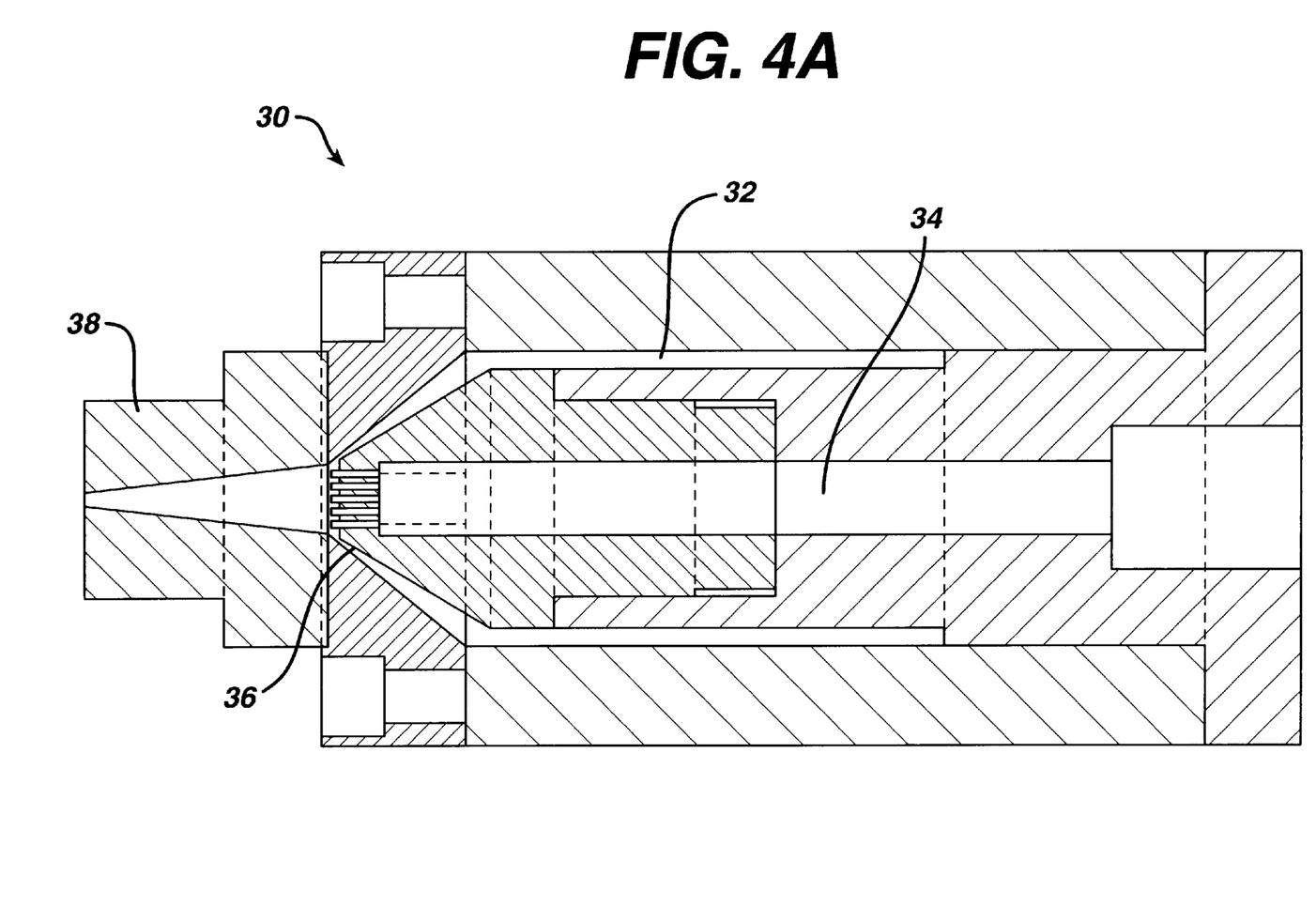

A coextrusion die suitable for use in forming the islands in the sea configuration (FIG. 2B) is shown in FIGS. 4 and 4A. Coextrusion die 30 includes a bore 32 for flow of sheath polymer, a bore 34, a "volcano plate" die 36 having apertures constructed to form the "islands", and a converging foam die 38. The die land length is preferably very short, so that the L/D ratio of the die is less than 5:1, preferably less than 1:1. Also, the entrance angle from the barrel to die is preferably high, e.g., from 60 to 180 degrees, more preferably about 140 degrees. These parameters produce a sudden pressure drop at the die that produces a well controlled foam. Suitable dies are discussed in copending U.S. Ser. No. 08/699,891, incorporated by reference above.

Other embodiments are within the claims.

For instance, while bicomponent filaments have been described above in the Detailed Description, the filaments can contain any desired number of components, and in this case are manufactured by extrusion through a suitable multicomponent die using the appropriate number of extruders. In this case, more than one of the components can be foamed. For example, the floss can include a non-foamed core, an intermediate soft foam layer, and an outer, thin foam layer. The outer thin foam layer can include impart a desired property, e.g., surface roughness, without compromising the softness provided by the intermediate foam layer. The outer foam layer can also be heavily loaded with an additive such as an abrasive, flavor or the like, without sacrificing the mechanical or other desired properties of the floss.

Example 1

Three "islands in the sea" cross-section round flosses were made using XL 1092-2 polymer from M.A. Hanna as the core component (34 islands) and KRATON TPE (60 Shore A hardness) as the sheath component (sea). The three flosses were identical except for their volumetric ratios of sheath to core, which were as follows: 25/75, 50/50, 75/25. 1% of a chemical blowing agent (Hydrocerol BIH) was added to the KRATON TPE to foam the sheath component.

The zone temperatures of the foam extruder were as follows: feeding zone 170° C.; melting and mixing zones 190° C.; compression (cooling) zone 160° C.; die 170° C. The zone temperatures of the sheath component extruder were as follows: feeding zone 170° C.; melting and mixing zones 190° C.; compression (cooling) zone 180° C.; die 170° C. The extruder speed was 5–10 rpm. The floss was pre-cooled at the die exit by a stream of compressed air, to obtain a desired surface roughness, and was then cooled in a water bath. The cooled floss was wound at very low (close to zero) tension. The final diameter of the floss was about 90 mil.

The above process was repeated, replacing the chemical blowing agent with a physical blowing agent ($CO_2$ gas). The gas feeding pressure was 600–800 psi. The amount of gas was about 15 g/min at 10 rpm extruder speed.

All of the flosses exhibited desirable surface roughness characteristics and good tensile strength.

What is claimed is:

1. A dental floss comprising a filament that includes a foam outer layer and a reinforcing core, said reinforcing core comprising a non-foamed thermoplastic elastomer.

2. The dental floss of claim 1 wherein said foam outer layer is continuous along the length of the floss.

3. The dental floss of claim 1 wherein said foam outer layer surrounds said reinforcing core in a sheath/core configuration.

4. The dental floss of claim 1 wherein said foam outer layer comprises a foamed thermoplastic elastomer.

5. The dental floss of claim 1 wherein said foam outer layer is formed of a polymer having a hardness of 0–85 Shore A prior to foaming.

6. The dental floss of claim 1 wherein said foam outer layer comprises a styrene-butadiene block copolymer.

7. The dental floss of claim 1 wherein said dental floss has a tensile strength of at least 2000 g.

8. The dental floss of claim 7 wherein said dental floss has a tensile strength of at least 2600 g.

9. The dental floss of claim 1 wherein said foam outer layer includes an additive that is released from the floss during use.

10. The dental floss of claim 9 wherein said additive is selected from the group consisting of colors, fragrances, flavors and active ingredients.

11. A method of making a filament comprising:
 (a) coextruding two or more polymers to form a multi-component dental floss filament; and
 (b) foaming one of said polymers before or during coextrusion to form a foamed outer layer on said filament.

12. The method of claim 11 wherein said foaming step comprises injecting a gas into the polymer to be foamed while the polymer is in a molten state.

13. The method of claim 11 wherein said foaming step comprises adding a chemical blowing agent to the polymer to be foamed.

14. The method of claim 11 wherein coextruding step includes coextruding a first non-foamed polymer as an inner core and the foamed polymer as a sheath surrounding said core.

15. The method of claim 11 wherein said coextruding step includes to extruding a first non-foamed polymer as a plurality of filaments and the foamed polymer as a sheath surrounding said filaments, forming a floss having an islands-in-the-sea configuration.

16. The method of claim 11 further comprising the step of incorporating an additive into the foamed outer layer.

17. The method of claim 16 wherein said additive is incorporated after the foaming step.

18. The method of claim 16 wherein the additive is selected from the group consisting of colors, fragrances, flavors and active ingredients.

19. The method of claim 16 wherein the additive is incorporated in a manner to allow it to be released from the floss during use.

20. The method of claim 11 wherein said polymers are selected to allow said filament to be used as a dental floss.

21. A method of flossing the teeth of a mammal by inserting between two teeth of the mammal a length of a dental floss comprising a foam outer layer and a reinforcing core, said reinforcing core comprising a non-foamed thermoplastic elastomer.

22. A dental floss comprising a filament that includes an open cell foam outer layer and a reinforcing core, said reinforcing core comprising a non-foamed thermoplastic elastomer.

23. A dental floss comprising a filament that includes a foam outer layer and a reinforcing core wherein said filament comprises a plurality of reinforcing core elements arranged within the foam outer layer in an islands-in-the-sea configuration.

24. The dental floss of claim 23 wherein said foam outer layer is continuous along the length of the floss.

25. The dental floss of claim 23 wherein said reinforcing core comprises a non-foamed thermoplastic elastomer.

26. The dental floss of claim 23 wherein said foam outer layer comprises a foamed thermoplastic elastomer.

27. The dental floss of claim 23 wherein said foam outer layer is formed of a polymer having a hardness of 0–85 Shore A prior to foaming.

28. The dental floss of claim 23 wherein said foam outer layer comprises a styrene-butadiene block copolymer.

29. The dental floss of claim 23 wherein said dental floss has a tensile strength of at least 2000 g.

30. The dental floss of claim 23 wherein said foam outer layer includes an additive that is released from the floss during use.

31. The dental floss of claim 30 wherein said additive is selected from the group consisting of colors, fragrances, flavors and active ingredients.

32. The dental floss of claim 23 wherein said foam outer layer comprises an open cell foam.

33. The dental floss of claim 1 wherein said foam outer layer comprises an open cell foam.

34. The method of claim 21 wherein said foam outer layer is continuous along the length of the floss.

35. The method of claim 21 wherein said reinforcing core comprises a non-foamed thermoplastic elastomer.

36. The method of claim 21 wherein said foam outer layer comprises a foamed thermoplastic elastomer.

37. The method of claim 21 wherein said foam outer layer is formed of a polymer having a hardness of 0–85 Shore A prior to foaming.

38. The method of claim 21 wherein said foam outer layer comprises a styrene-butadiene block copolymer.

39. The method of claim 21 wherein said dental floss has a tensile strength of at least 2000 g.

40. The method of claim 21 wherein said foam outer layer includes an additive that is released from the floss during use.

41. The method of claim 40 wherein said additive is selected from the group consisting of colors, fragrances, flavors and active ingredients.

42. The method of claim 21 wherein said foam outer layer comprises an open cell foam.

43. A method of flossing the teeth of a mammal by inserting between two teeth of the mammal a length of a dental floss comprising a filament that includes a foam outer layer and a reinforcing core wherein said filament comprises a plurality of reinforcing core elements arranged within the foam outer layer in an islands-in-the-sea configuration.

* * * * *